US012636431B2

(12) United States Patent
O'Connor et al.

(10) Patent No.: US 12,636,431 B2
(45) Date of Patent: *May 26, 2026

(54) DRUG DELIVERY INSERTION APPARATUSES AND SYSTEM

(71) Applicant: INSULET CORPORATION, Acton, MA (US)

(72) Inventors: Jason O'Connor, Acton, MA (US); Ian McLaughlin, Groton, MA (US); Daniel Allis, Boxford, MA (US); David Nazzaro, Groveland, MA (US)

(73) Assignee: INSULET CORPORATION, Acton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/643,990

(22) Filed: Apr. 23, 2024

(65) Prior Publication Data

US 2024/0269379 A1 Aug. 15, 2024

Related U.S. Application Data

(63) Continuation of application No. 16/515,749, filed on Jul. 18, 2019, now Pat. No. 11,992,653.

(60) Provisional application No. 62/699,805, filed on Jul. 18, 2018.

(51) Int. Cl.
| | |
|---|---|
| *A61M 5/145* | (2006.01) |
| *A61M 5/142* | (2006.01) |
| *A61M 5/158* | (2006.01) |
| *A61M 5/162* | (2006.01) |
| *A61M 5/168* | (2006.01) |

(52) U.S. Cl.
CPC .... *A61M 5/14566* (2013.01); *A61M 5/14248* (2013.01); *A61M 5/1582* (2013.01); *A61M 5/162* (2013.01); *A61M 5/16881* (2013.01); *A61M 2005/14252* (2013.01); *A61M 2205/3379* (2013.01); *A61M 2205/583* (2013.01)

(58) Field of Classification Search
CPC .... A61M 2005/14268; A61M 5/31591; A61M 5/31578; A61M 5/3158; A61M 5/31563
See application file for complete search history.

(56) References Cited

U.S. PATENT DOCUMENTS

| | | | | |
|---|---|---|---|---|
| 3,325,061 A | * | 6/1967 | Ellsworth | ........... A61M 5/3137 D24/114 |
| 3,563,240 A | * | 2/1971 | Silver | .................... A61M 3/005 604/211 |
| 4,153,056 A | * | 5/1979 | Silver | ............... A61M 5/31551 604/222 |
| 4,275,729 A | * | 6/1981 | Silver | ............... A61M 5/31551 604/211 |

(Continued)

*Primary Examiner* — Scott J Medway
(74) *Attorney, Agent, or Firm* — Goodwin Procter LLP

(57) ABSTRACT

Disclosed are examples for a system for drug delivery and components thereof. The system may include an on-body pump device and a secondary unit. The on-body pump device may include a reservoir and a fluid pathway. The reservoir may be configured to hold a liquid drug. The secondary unit may be removably coupled to the on-body pump device. The secondary unit may be configured to receive a prefilled cartridge containing a liquid drug, expel the liquid drug from the prefilled cartridge, and deliver the liquid drug to the reservoir of the on-body pump device via the fluid pathway. Examples of variations to the secondary unit are also disclosed.

12 Claims, 8 Drawing Sheets

(56)                  References Cited

U.S. PATENT DOCUMENTS 4,357,971 A  *  11/1982  Friedman ............ A61M 5/1782
                                                               604/218
4,563,178 A  *   1/1986  Santeramo .......... A61M 5/1782
                                                                141/27
4,592,742 A  *   6/1986  Landau ................... A61M 5/30
                                                               604/71
4,654,035 A  *   3/1987  Ando ................ A61M 5/31555
                                                               604/210
4,846,797 A  *   7/1989  Howson .............. A61M 5/1456
                                                               604/154
4,874,385 A  *  10/1989  Moran .............. A61M 5/31555
                                                               604/210
4,946,441 A  *   8/1990  Laderoute ............ A61J 1/1406
                                                               604/218
5,095,914 A  *   3/1992  Sarstedt .......... A61B 5/150244
                                                               604/220
5,139,484 A  *   8/1992  Hazon ................. A61M 5/1456
                                                               604/154
5,344,409 A  *   9/1994  Ennis, III ......... A61M 5/31591
                                                               604/210
5,728,075 A  *   3/1998  Levander ............ A61M 5/2448
                                                               604/211
5,830,187 A  *  11/1998  Kriesel ................ A61M 5/152
                                                               604/890.1
6,074,372 A  *   6/2000  Hansen ............ A61M 5/31525
                                                               604/211
6,113,578 A  *   9/2000  Brown ................. G01F 11/029
                                                                222/23
6,231,550 B1 *   5/2001  Laughlin ............ A61M 5/3148
                                                               604/187

6,340,357 B1 *   1/2002  Poulsen .................. A61M 5/20
                                                               604/154
7,261,704 B2 *   8/2007  Tachikawa .......... A61M 5/3158
                                                               604/187
7,329,241 B2 *   2/2008  Horvath ............ A61M 5/31555
                                                               604/208
7,470,259 B2 *  12/2008  Hoyle, Jr. ........... A61M 5/2429
                                                               604/209
7,753,890 B2 *   7/2010  Lafferty, IV ......... A61M 5/001
                                                               604/68
7,785,297 B2 *   8/2010  Miller ............... A61M 5/31553
                                                               604/71
8,465,460 B2 *   6/2013  Yodfat .............. A61M 5/14244
                                                               604/151
8,568,361 B2 *  10/2013  Yodfat ............... A61M 5/1456
                                                               604/152
8,773,660 B2 *   7/2014  Pommereau ...... A61M 5/14566
                                                               356/343
9,186,463 B2 *  11/2015  Hoyle, Jr. ........... A61M 5/3158
9,486,574 B2 *  11/2016  Yodfat ............. A61M 5/14248
9,724,479 B2 *   8/2017  Sutkin .............. A61M 5/31581
10,149,947 B2 *  12/2018  Bayer .............. A61M 5/31585
10,391,253 B1 *   8/2019  Joseph ............. A61M 5/31528
10,729,618 B2 *   8/2020  Yaegashi ............. A61J 1/2048
2003/0139774 A1 *   7/2003  Epstein ........... A61B 17/00491
                                                               604/82
2005/0215957 A1 *   9/2005  Hynes .............. A61M 5/31551
                                                               604/218
2008/0119790 A1 *   5/2008  Hawkins .......... A61M 5/14248
                                                               604/131
2015/0157537 A1 *   6/2015  Lanigan ............... G01F 11/086
                                                               141/349
2020/0345929 A1 *  11/2020  Ben-David ........ A61M 5/1452

* cited by examiner

A-A OPTION 1

B-B OPTION 1 BB

A-A OPTION 2

B-B OPTION 2

DRUG DELIVERY INSERTION APPARATUSES AND SYSTEM

CROSS-REFERENCE TO RELATED APPLICATION

This application is a continuation of U.S. patent application Ser. No. 16/515,749, filed Jul. 18, 2019, which claims priority to U.S. Provisional Patent Application No. 62/699,805, filed Jul. 18, 2018, the entire contents of which are incorporated herein by reference in their entirety.

BACKGROUND

Presently wearable drug delivery devices may be large and intrusive and as a result may be uncomfortable for a user to wear. In addition, operation of the drug delivery device and filling the drug delivery device with the required drugs may be complicated and require dexterity. A number of users may lack the dexterity to fill and operate the drug delivery device. It would be advantageous for there to be a drug delivery system that provides the capability to easily fill an on-body pump device that is small and non-intrusive.

SUMMARY

Disclosed is an example of a system that includes an on-body pump device and a secondary unit. The on-body pump device may include a reservoir and a fluid pathway. The reservoir may be configured to hold a liquid drug. The secondary unit may be removably coupled to the on-body pump device. The secondary unit may be configured to receive a prefilled cartridge containing a liquid drug, expel the liquid drug from the prefilled cartridge, and deliver the liquid drug to the reservoir of the on-body pump device via the fluid pathway.

Disclosed is an on-body pump device including a first reservoir, a second reservoir, a first pump mechanism, a second pump mechanism, a flow regulator valve and a cannula. The first reservoir may be configured to hold a first fluid. The second reservoir configured to hold a second fluid. The first pump mechanism may be fluidly coupled to the first reservoir and may be operable to pump the first fluid from the first reservoir at a first preset rate. The second pump mechanism may be fluidly coupled to the second reservoir and may be operable to pump the second fluid from the second reservoir at a second preset rate. The flow regulator valve may be fluidly coupled to the first pump mechanism and the second pump mechanism. The flow regulator valve may comprise a first flow channel and a second flow channel. The cannula may be fluidly coupled to the flow regulator valve.

Disclosed is a secondary unit including an opening, a needle insertion mechanism and a settings dial. The opening may be configured to receive a prefilled cartridge containing a liquid drug. A fill needle and a cartridge stop may be within the opening. The needle insertion mechanism may be configured to actuate an introducing needle device of an on-body pump device. The settings dial may be configured to set or adjust an amount of the liquid drug for delivery into the on-body pump device. The fill needle may be configured to pierce a septum of the on-body pump device to deliver the liquid drug to the on-body pump device.

DETAILED DESCRIPTION

Examples disclosed herein provide techniques and a drug insertion delivery apparatus usable in a drug delivery system. Example of a disclosed drug delivery system include an on-body pump device and a removable secondary unit/assembly. The disclosed secondary unit may be configured to include various components typically maintained in a housing of prior on-body pump devices, and, as a result, the disclosed on-body pump device of the drug delivery system described herein may be made to be smaller, more light-weight, and have fewer internal components.

Figure 1:
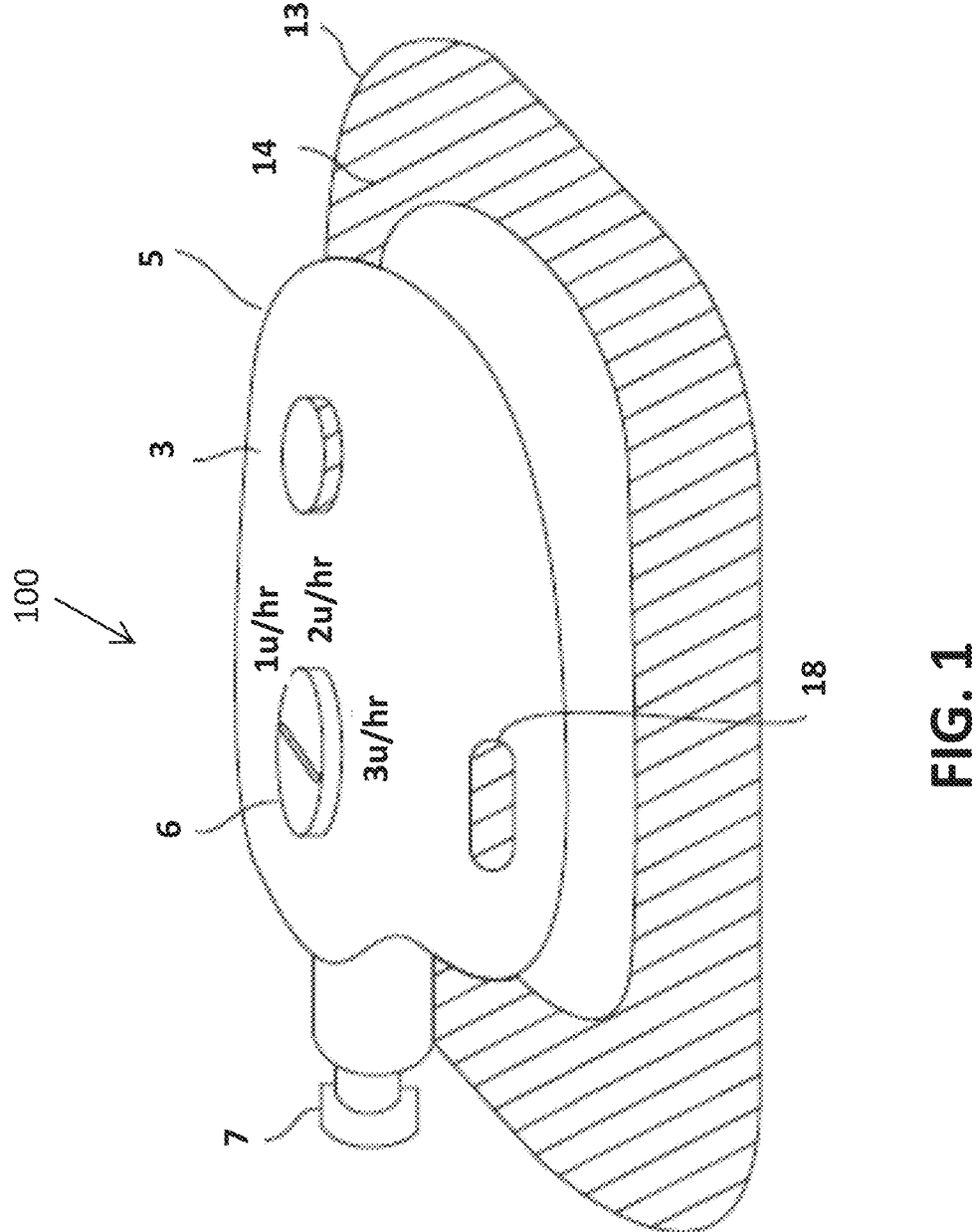
FIG. 1 illustrates an example of a drug delivery system.

As shown in FIG. 1, an example of a drug delivery system 100 may include an on-body pump device (or drug delivery device) 14 and a secondary unit 5 or assembly coupled to the on-body pump device 14. The secondary unit 5 may include a settings dial 6, a needle insertion mechanism button 3, and a release button 18. The on-body pump device 14 may be a wearable device and may be disposable. For example, the on-body pump device 14 may be affixed to the body (typically, the skin) of a user via an adhesive pad 13. Of course, methods other than adhesive pad 13 may be used to affix the on-body pump device 14 to the body of the user. As an alternative, adhesive pad 13 may be a base a semi-permanently attached to the body of the user and the on-body pump device 14 may be configured to removably couple to the semi-permanently attached base, or the like.

The secondary unit 5 may include internal components (shown in other examples) for expelling a liquid drug from a liquid drug source, such as a prefilled cartridge 7, and delivering the liquid drug to a reservoir (shown in other examples) in the on-body pump device 14. The prefilled cartridge 7 is shown inserted into an opening (shown in other examples) of the secondary unit 5. After filling the reservoir of the on-body pump device 14, the secondary unit 5 may be removed/decoupled from the on-body pump device 14. The settings dial 6 of the secondary unit 5 may be operable to set or adjust operation of the on-body pump device (e.g., set or adjust dosages and/or flow rates of the liquid drug from the reservoir of the on-body pump device 14). In addition, the insertion mechanism button 3 of the secondary unit 5 may actuate a needle insertion mechanism that operates to cause an introducing needle device (shown in the example of FIG. 3) to insert a needle coupled to the reservoir into the skin of a user (i.e., a wearer) of the on-body pump device 14. The configuration of the secondary unit 5 is beneficial and advantageous because it enables the on-body pump device 14 to be smaller and include fewer components than prior pump devices.

In an example, the on-body pump device 14 may include a reservoir for the liquid drug, a fluid path to a user, and/or a drive mechanism for delivering the liquid drug from the reservoir to the user through the fluid path. The on-body pump device may be mechanically operated or may include one or more electromechanical systems.

Various examples described herein provide a smaller on-body pump device (e.g., a wearable drug delivery device including a drug pump) that may be filled by a prefilled cartridge 7. In various examples, the secondary unit 5 may be removable from the on-body pump device 14 and may be configured to operate with either a mechanical or electromechanical on-body pump device 14. The removable secondary unit 5 may be attached to the top of the on-body pump device 14. In some instances, the removable secondary unit 5 may be removed after the pump device is filled with a liquid drug from the prefilled cartridge and a needle insertion mechanism is deployed. This arrangement (e.g., on-body pump device 14 and removable secondary unit 5) may enable the needle insertion mechanism to be moved to the secondary unit 5 to further reduce the size of the on-body pump device 14 as compared to prior wearable pumps.

The secondary unit 5 may also incorporate a fill mechanism (described with reference to another example) to allow for variable filling of the on-body device from a prefilled cartridge. The drug delivery system 100 may also allow for selecting customizable drug delivery parameters such as a basal rate and/or a bolus increment size. The on-body pump device 14 may include a bolus button that delivers a bolus of fluid (e.g., liquid drug) per each button push. The amount of fluid provided per each button push may be selected or adjusted by the system (e.g., as set during manufacture or by the patient/user).

The secondary unit 5 may, for example, be used for any combination of filling the on-body pump device 14, housing or triggering a needle insertion mechanism, setting adjustable parameters such as basal rates or bolus increments, and/or activating the on-body pump device 14 either mechanically or electronically.

As described with reference to other examples, the secondary unit 5 may have multiple interlocks that require the reservoir of the on-body pump device to be filled before the needle insertion mechanism may be triggered and/or require the needle insertion mechanism be deployed before the secondary unit may be removed from the on-body pump device. In other examples, the secondary unit is removable from the on-body pump device and may include a number of mechanisms and/or components for filling a reservoir of the on-body pump device.

In addition, the secondary unit may include a number of mechanisms and/or components configured to manage operation of the on-body pump device. As shown in the example of FIG. 1, the secondary unit 5 may include one or more setting dials, such as setting dial 6, that may be used to set a combination of variable settings. For example, a first dial, such as setting dial 6, may be operable to select a basal rate, and a second dial (not shown in the example of FIG. 1) may be operable to select bolus increments. In the example, the first and second dials may interact with the on-body pump device 14 through a common septum or respective individual septa in the surface of the on-body pump device 14.

Figure 2:
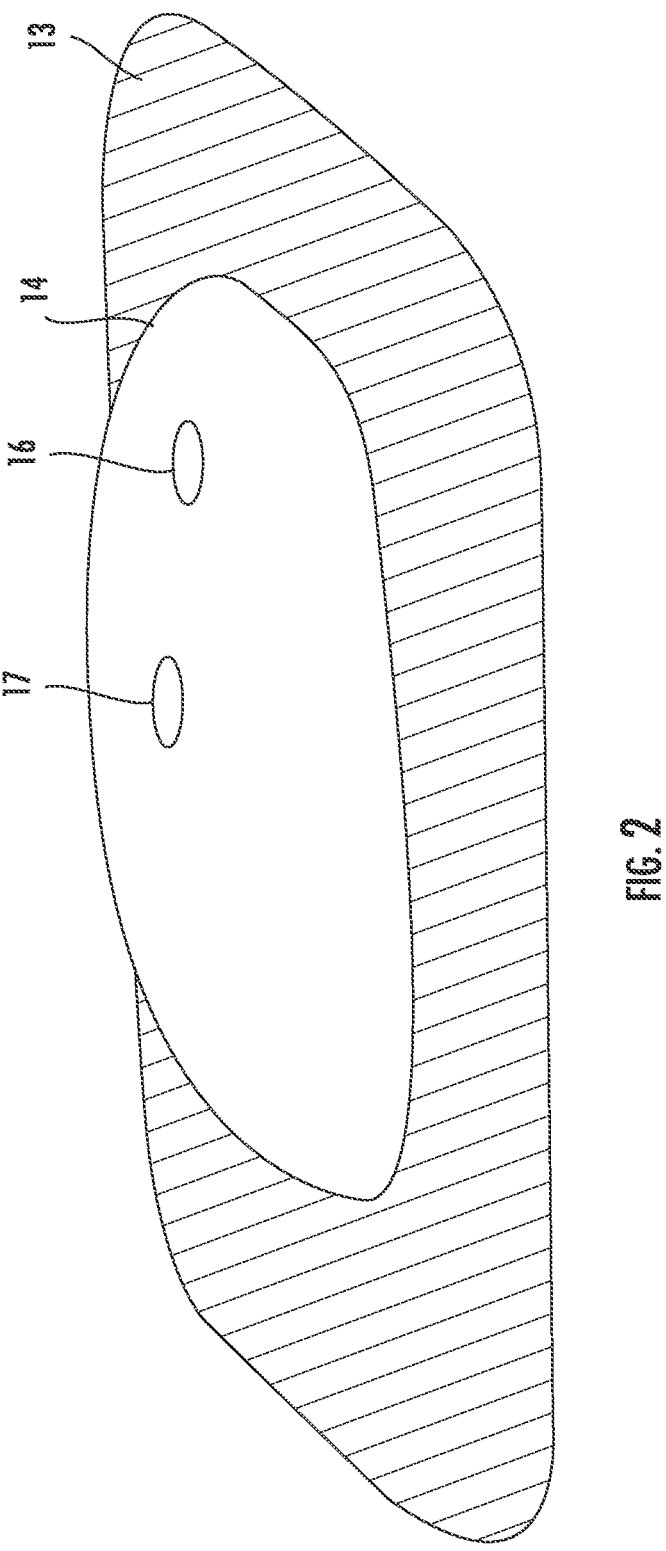
FIG. 2 illustrates an example of an on-body pump device.

FIG. 2 illustrates an example of an on-body pump device. In the example, a first individual septum 16 and a second individual septum 17, both of which may be self-sealing, for example, when the secondary unit 5 is removed from the on-body pump device 14 are shown. The on-body pump device 14 is held in place by adhesive pad 13. The respective septa 16 and 17 may interact or interface with components of the secondary unit 5 as described in more detail below.

Figure 3:
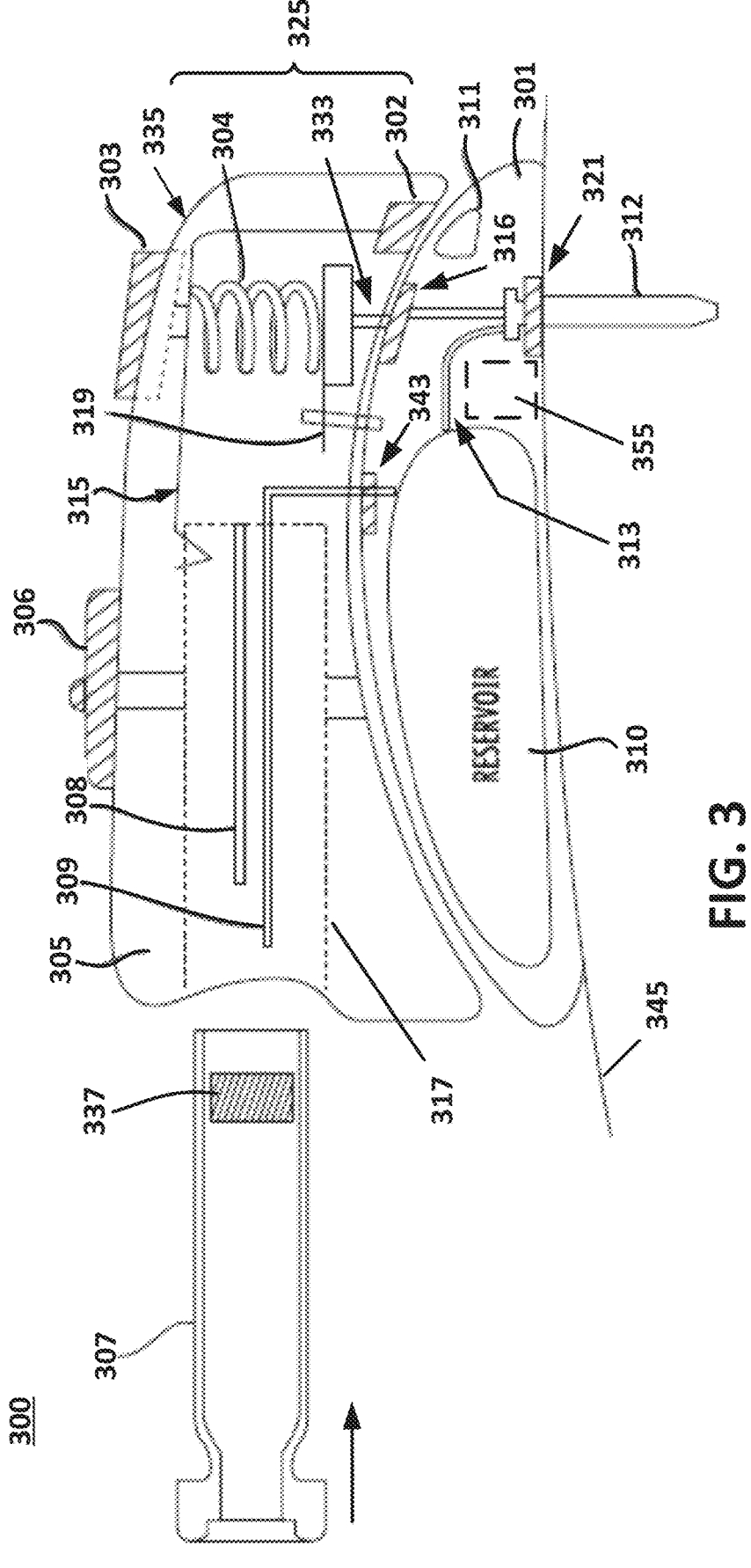
FIG. 3 illustrates a side view of an example of a drug delivery system.

FIG. 3 illustrates a side view of an example of a drug delivery system 300. The drug delivery system 300 includes an on-body pump device 301 and a secondary unit 305. The on-body pump device 301 and the secondary unit 305 are shown coupled together.

The on-body pump device 301 may include a reservoir 310, an introducing needle device 321, a fill septum 343, a septum 316, a fluid pathway 313, a drive or pump mechanism 355 and an activation component 311.

The secondary unit 305 may include, for example, an opening 317, an activation switch 302, a needle insertion mechanism 325, and other components.

The activation switch 302 may interact with the activation component 311 of the on-body pump device 301 to provide electronic or mechanical activation of the secondary unit 305 and the on-body pump device 301. For example, the activation switch 302, which may be a mechanical switch or a reed switch, may be triggered by an insertion mechanism, a filling process, attachment of the secondary unit 305 from the on-body pump device 301, or removal of the secondary unit 305 from the on-body pump device 301.

The opening 317, for example, may be configured to receive a prefilled cartridge such as 307 containing a liquid drug (not shown). In the example, the opening 317 may include a fill needle 309 and a cartridge stop 308.

The needle insertion mechanism 325 may be configured to actuate the introducing needle device 321 of the on-body pump device 301. The needle insertion mechanism 325 may include an insertion mechanism button 303, an insertion spring 304 and a member 333 coupled to the insertion spring 304.

In an example, filling of a reservoir 310 of the on-body pump device 301 may be performed by placing a prefilled cartridge 307 into an opening 317 of the secondary unit 305. The prefilled cartridge 307 may contain a liquid drug or other medicinal fluid. When the prefilled cartridge 307 is placed into the secondary unit 305, at first end of the fill needle 309 may pierce a plunger 337 of the cartridge 307. An opposite end of the fill needle 309 may be configured to pierce the fill septum 343 of the on-body pump device 301 to fill the reservoir 310. In an alternative example, the fill needle 309 may be fluidly coupled to another needle that is configured to pierce the fill septum 343. As the cartridge 307 is pushed further into the opening 317 of the secondary unit 305, the cartridge plunger 337 contacts a stop 308, preventing the cartridge plunger 337 from moving further into the opening 317 while pushing the liquid drug in the cartridge 307 through the fill needle 309. As the prefilled cartridge is pushed further into the opening 317 and the stroke is completed, interlock 315 (e.g., detent(s) or other mechanisms) in the opening 317 of the secondary unit 305 may interact and lock with the cartridge 307 within the opening 317, which gives the user positive feedback of full fill (i.e., of the reservoir 310) and may prevent removal of the cartridge 307 from the secondary unit 305. This may also allow for no sharps to be exposed after fill is complete or prevent reuse of secondary unit 305.

In addition, the secondary unit 305 may include a settings dial 306 and an insertion mechanism button 303 that are located at the surface 335 of the secondary unit 305. The settings dial 306 may be configured to set or adjust an amount of liquid drug for delivery from the cartridge 307 into the reservoir 310 of the on-body pump device 301.

The drive or pump mechanism 355 may be operable to pump the liquid drug or fluid from the reservoir 310 to the fluid pathway 313 to the cannula 312 for delivery of the liquid drug or fluid according to the settings provided via the settings dial 306. For ease of illustration, the couplings of the pump mechanism 355 to the fluid pathway 313 or the reservoir 310, and the introducing needle device 321 are not shown. The fill volume of the liquid drug or fluid that is delivered to the reservoir 310 may be set based on a setting of the setting dial 306. The pump mechanism 355 may be a mechanical pump or an electromechanical device. The pump mechanism 355 may be powered by batteries or another power source. The pump mechanism 355 may be a component as known in the art.

In a further example, the interlock 315 may prevent the needle insertion mechanism 325 from being actuated until the cartridge is locked in the opening 317 by the interlock 315. The introducing needle device 321 of the on-body pump device 301 may not function until the activation component 311 is actuated by proper placement of actuation activation switch 302 in or near activation component 311. In the example, the interlock 315 when actuated by the cartridge 307 may enable the needle insertion mechanism 325 to operate. The interlock 315 may also actuate activation switch 302, which, in turn, actuates activation component 311 of the on-body pump device 301. Actuation of the activation component 311 may enable the introducing needle device 321 to operate as well. For example, introducing needle device 321 may be operable to insert a needle coupled to the reservoir into the skin of a user (i.e., a wearer) of the on-body pump device 301.

The fill needle 309 may be coupled to a reservoir 310 (e.g., a bag reservoir) positioned in the on-body pump device 301. As the cartridge 307 is pushed into the secondary unit 305, the liquid drug (not shown) stored in the cartridge 307 may be expelled and delivered to the reservoir 310 through the fill needle 309.

Activation of the on-body pump device 301 may be prevented during the filling process. For example, activation of the needle insertion mechanism 325 may be prevented until after the filling process is complete. In various examples, after the reservoir 310 has been filled and the cartridge 307 has been emptied, the interlock 315 may be triggered allowing the insertion mechanism button 303 to be unlocked and allow the user to press an activation button when ready. For example, prior to completing the filling process, the interlock 315 may remain in a locked state preventing the insertion mechanism from firing. The interlock 315 may also be used to activate one or more electrical components of the on-body pump device through, for example, a mechanical switch or a reed switch. In various examples, a device removal interlock, such as 319, may be triggered by the fill action if the secondary unit does not incorporate the insertion mechanism. For example, the device removal interlock 319 may be a spring plunger-like mechanism or the like.

In various examples, deployment or activation of the insertion mechanism 325 may be regulated by one or more interlocks. For example, once the fill interlock 315 has been actuated or released and the user has placed the on-body pump device onto her body, the insertion mechanism 325 may be triggered by the insertion mechanism button 303. In addition, before the insertion mechanism button 303 may be pressed, the device removal interlock 319 may require the on-body pump device 301 to be on the user's body. In various examples, the device removal interlock 319 may be housed in the secondary unit 305 coupled to a member 333 or component passing through the waterproof seal (e.g., septum) 316. The member 333 may move the cannula 312 (also referred to as a cannula/needle) into the skin 345 of the user and may retract the needle, leaving the cannula 312 in the skin 345 to provide access to the user for delivery of the liquid drug. In various examples, the cannula/needle 312 may be inserted from the introducing needle mechanism 321 that remains in the skin.

In various examples, one or more of the components of the insertion mechanism 325 may be housed in the secondary unit. Alternatively, one or more of the insertion mechanism 325 components may be housed in the on-body pump device 301 and the secondary unit 305 may house the corresponding components for providing mechanical energy, such as spring 304, for activating the needle insertion mechanism 325. For example, the on-body pump device 301 may house the needle and cannula 312 while the secondary unit 305 houses one or more components (e.g., a spring 304) for firing the needle and cannula. After access to the user is provided by puncturing the skin 345, the needle insertion mechanism 325 may trigger the device removal interlock 319 that may activate a drive mechanism (not shown in this example) for expelling the liquid drug from the 310 reservoir for delivery into the skin 345 of the user. The drive mechanism may be a mechanical system or an electromechanical system (e.g., a pump system). The device removal interlock 319 may also enable the secondary unit 305 to be removed from the on-body pump device 301 or may allow the secondary unit 305 to be removed by engaging a release button 18 (not shown in this example). In various examples, activation of the mechanical or electromechanical drive system (not shown in this example) may be triggered (or allowed to be triggered) after completion of the filling process, after completion of a needle/cannula insertion process, and/or removal of the secondary unit 305 from the on-body pump device 301 (or any combination thereof).

Figure 4:
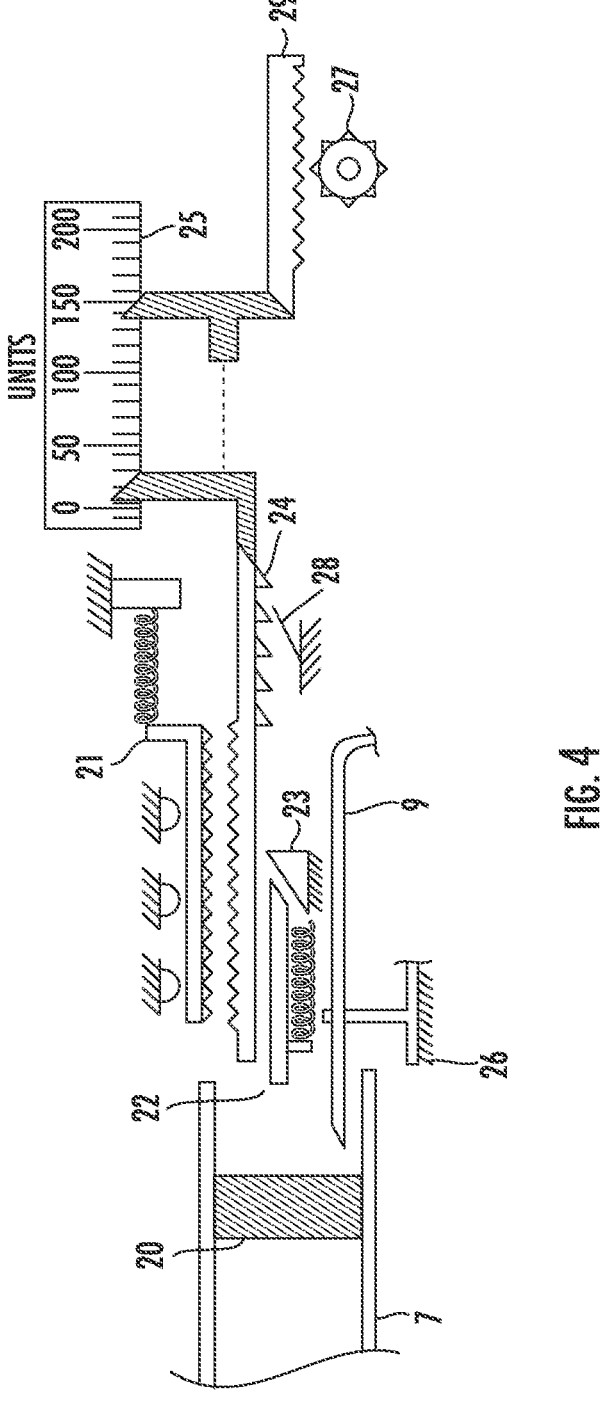
FIG. 4 illustrates an example of a mechanism that enables variable filling of an example of an on-body pump device.

In various examples, the drug delivery system 300 described in the example of FIG. 3 may provide for variably filling the reservoir of the on-body pump device via a variable fill mechanism. FIG. 4 illustrates an example of a mechanism that enables variable filling of an example of an on-body pump device.

In the example of FIG. 4, the variable fill mechanism 400 enables a user to variably fill the reservoir, such as 310 of FIG. 3, of an on-body pump device, such as 301, to a desired volume and to not necessarily have all of the liquid drug contained in the prefilled cartridge transferred to the reservoir. Variable fill also allows a user to use one or more cartridges to fill the on-body pump device. In such an example, the interlock 315 described with reference to FIG. 3 does not prevent the cartridge from being removed from the opening 317.

In an example, a first on-body pump containing insulin, for example, may be filled with 250 units of a 300-unit cartridge. When removed, the cartridge may have 50 units remaining in the cartridge. A second on-body pump device may be filled with the remaining 50 units of the same 300-unit cartridge and may be filled further with additional units (e.g., 200 units) from a 300-unit second cartridge. The second 300-unit cartridge would then have 100 units remaining and could be used to partially fill a third on-body pump device. In another example, the same on-body pump device may be filled on separate occasions.

FIG. 4 illustrates examples of components that may enable variably filling an on-body pump. As an example, a user may set a required or desired fill volume using a dial, such as dial 6 of FIG. 1 or dial 306 of FIG. 3, on the secondary unit connected to a gear 27 operable to move a visual indicator 29 to the desired volume shown on a visual amount indicator component 25. The visual amount indicator component 25 may include a volume scale (e.g., "units") that shows a volume range of liquid drug that may be output by the variable fill mechanism 400. The visual indicator 29 shows an amount on the visual amount indicator component 25 that has been output by the variable fill mechanism 400. A needle 9 may be provided and is operable to pierce the movable plunger 20. For example, a user may push the prefilled cartridge 407 into the opening of the secondary unit (shown in previous examples) and the needle 9 pierces the movable plunger 20. The needle 9 may be supported or stabilized by a stabilizer component 26. The body of the prefilled cartridge 407 may contact a variable fill rod 21 which moves along with the prefilled cartridge 407. While the prefilled cartridge 407 is being pushed into the opening of the secondary unit, the movable plunger 20 pushes a travel pin 22 into a travel stop 23 having an inclined plane. The contact with the inclined plane of the travel stop 23 directs the travel pin 22 to contact the indicator rod 24. As a result of the contact, the travel pin 22 pushes the indicator rod 24 into contact with the variable fill rod 21. The variable fill rod 21 and the indicator rod 24 may, for example, have toothed edges as shown in FIG. 4 that are configured to mesh together. Of course, mechanical structures or mechanisms other than toothed edges may be used. As the cartridge 407 pushes the variable fill rod 21, the indicator rod 24 moves along with the cartridge 407. Once the cartridge stops being pushed into the opening in the secondary unit and the cartridge 407 is pulled out of the opening, a component 28 prevents the indicator rod 24 from being pulled back. For example, the component 28 may be spring-loaded or otherwise configured to prevent the indicator rod 24 from being pulled back.

If there is more fluid in the cartridge 407 than the requested volume shown on the visual indicator 29, then the indicator rod 24 may hit the hard stop 429 of the visual indicator 29 and prevent further fill. As the cartridge is pulled out, a spring-loaded travel pin 22 releases the connection between the spring-loaded variable fill rod 21 and the indicator rod 24. The spring-loaded variable fill rod 21 will return to its original position, ready for an additional cartridge to be inserted (if applicable). If the volume in the first cartridge is lower than the volume set by the user, a second cartridge may be inserted. Because the variable fill rod 21 may be spring-loaded, the variable fill rod 21 returns to its original position and the indicator rod 24 remains in place. Accordingly, the secondary unit 5 may be adjustable for any position of the plunger 20 within the cartridge 407.

In various examples, the secondary unit 5 may include an energy storage system (e.g., a spring system) that may be used for aiding the filling process. For example, in lieu of the user having to push the prefilled cartridge into the opening of the secondary unit 5, the user may place the prefilled cartridge into the secondary unit and actuate a button or the like to trigger the energy storage system which pushes the prefilled cartridge into the opening. The energy storage system may provide a force on the plunger within the prefilled cartridge to expel the liquid drug without the user needing to continue to push the prefilled cartridge. In the example of FIG. 4, the interlock 315 in the example of FIG. 3 may not be present or may not prevent removal of a cartridge.

Figure 5:
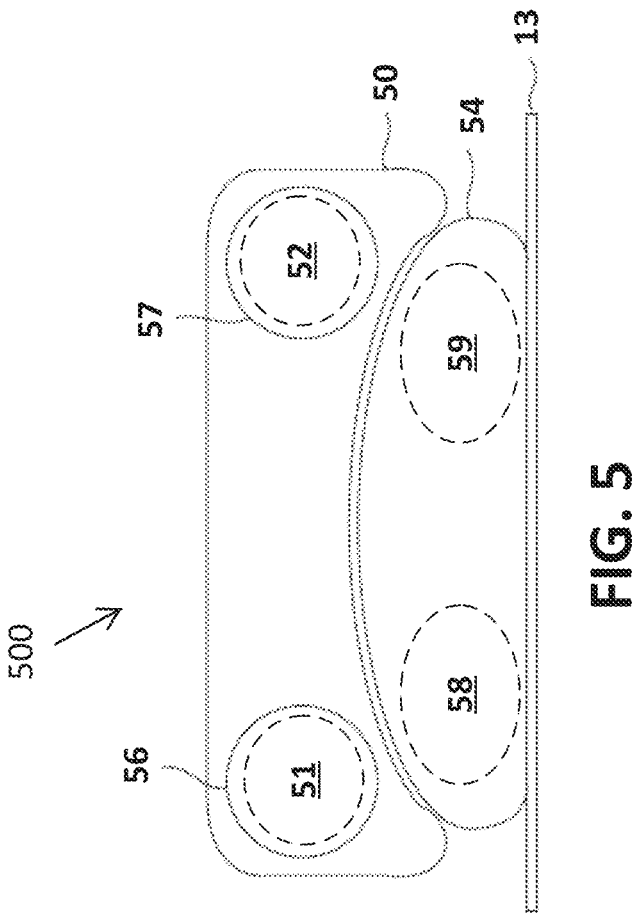
FIG. 5 illustrates another example of a drug delivery system.

FIG. 5 illustrates another example of a drug delivery system. As shown in FIG. 5, the drug delivery system 500 may include a removable secondary unit 50 and an on-body pump device 54. The secondary unit 50 may be configured differently than secondary unit 5 of previous examples. In the drug delivery system 500, the removable secondary unit

50 may have components like those of secondary unit 5 of FIG. 1, such as adhesive pad 13, setting dial 6, release button 18 and the like (some of which are not shown in this example), but may be further configured to accept two pre-filled cartridge vials for different types of fluid (e.g., insulin and glucagon, or some other combination of fluids). The first fluid cartridge 51 may be inserted into a first opening 56 and the second fluid cartridge 52 may be inserted into opening 57. Each cartridge 51 and 52 may fill separate reservoirs, for example, reservoirs 58 and 59, inside the on-body pump device 54 to be delivered to the patient in combination or at separate times. As an example, a first reservoir 58 may be configured for storing and delivering insulin and a second reservoir 59 would be configured for storing and delivering glucagon.

Figure 6:
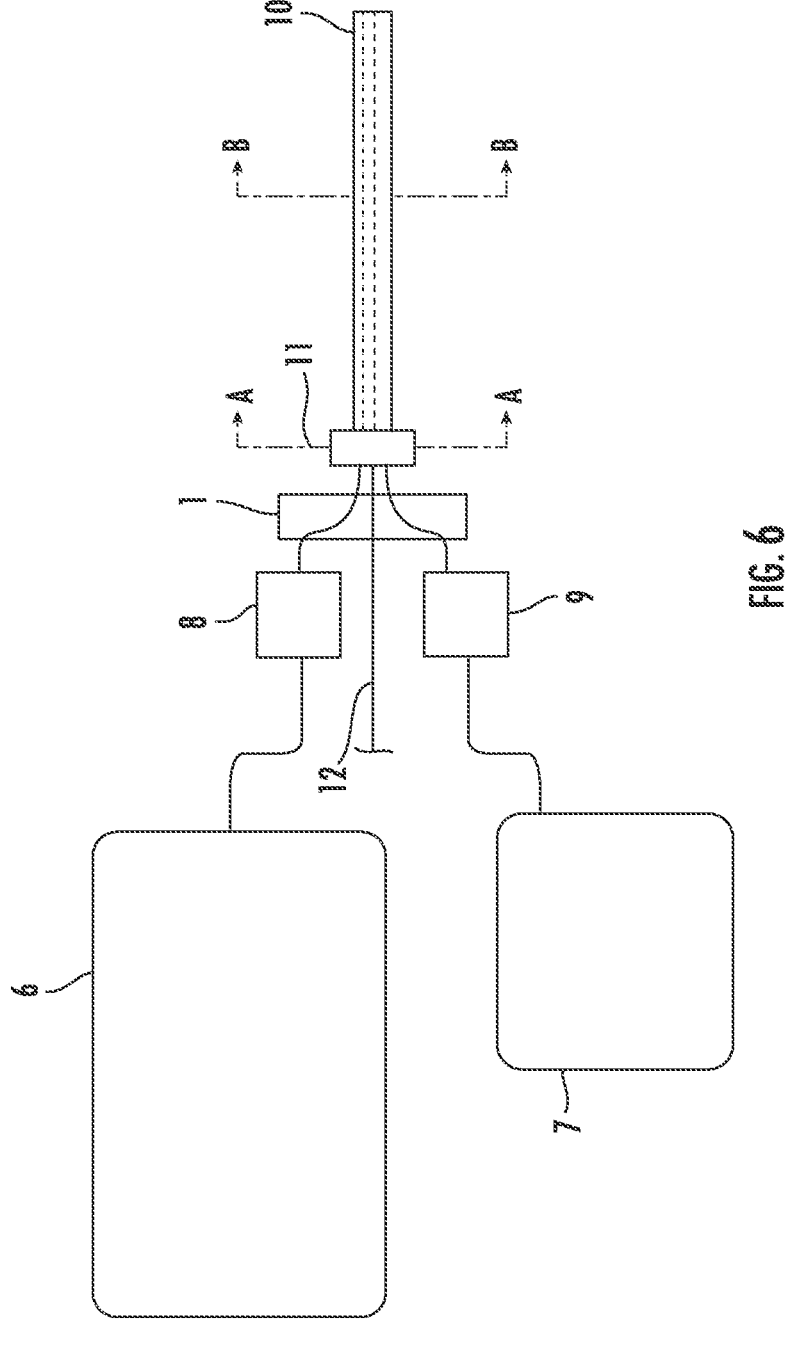
FIG. 6 illustrates a further example of a drug delivery system.

FIG. 6 illustrates a third example of a drug delivery system. The drug delivery system depicted in FIG. 6 may include a dual fluid delivery mechanism 600 that provides stored fluids to a user in one or more insertions/insertion sites. The on-body pump device may have two separate reservoirs 606 and 607. These reservoirs 606 and 607 may hold different fluids or the same type of fluid. The flow rates may be controlled by pump mechanisms 608 and 609 and/or by the flow regulator valve 601. The respective pump mechanisms 608 and 609 may be coupled to flow regulator valve 601 via respective fluid paths 621 and 622. The fluids may be delivered through separate cannulas (not shown) or through one insertion site via a multi-lumen cannula 610. The multi-lumen cannula 610 may have two or more ports (shown and described further with referent to the example of FIG. 7).

Figure 7:
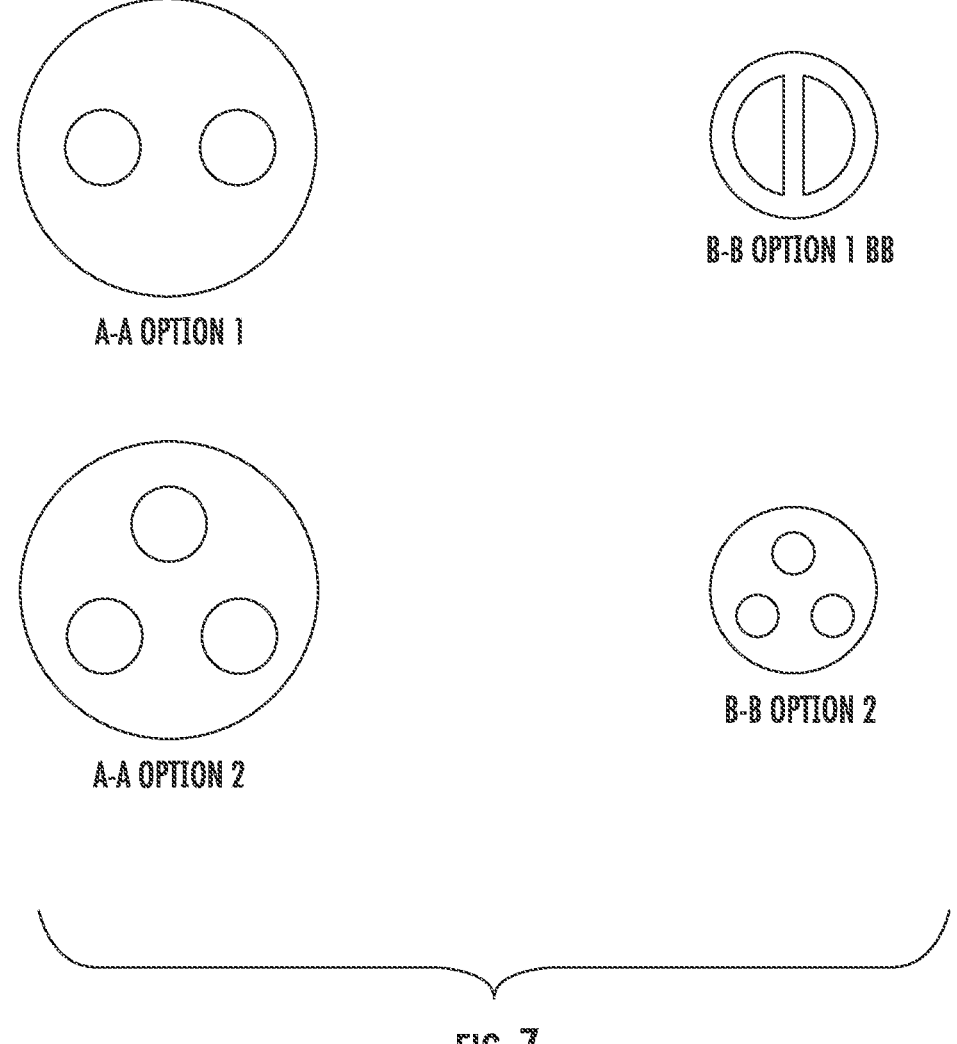
FIG. 7 illustrates cross-sections of various examples of multi-lumen cannulas that may be used with the drug delivery system example depicted in FIG. 6.

In one or more examples, the multi-lumen cannula 610 may deliver the fluid through the needle within the lumen, as shown in more detail with respect to FIG. 7. In FIG. 7, example configurations of multi-lumen cannula 610 are shown as viewed from either cross-section A-A or cross section B-B. As shown in the example of FIG. 7, the multi-lumen cannula 610 may have two ports where a first fluid is provided through a first port and a second fluid is provided through a second port. One of the two ports may also contain an introducing needle 612 used to pierce and lead the cannula into the skin of a user's body. In various examples, the multi-lumen cannula 610 may include three lumens where the two fluids are delivered through two separate lumens and the introducing or piercing needle 612 may be housed in a third lumen. The cannula 610 may have a nail head design that functions as a seal interface 611 to the fluid path as well as the needle 612.

FIG. 7 illustrates cross-sections of various exemplary multi-lumen cannulas that may be used with the drug delivery system depicted in FIG. 6. As shown, cross-section A-A option 1 may illustrate a cannula having two larger circular openings while cross-section BB, option 1 illustrates the cross-section farther along the cannula in which the cross-section has two half-circular openings for delivering the liquid drug. Similarly, cross-section A-A option 2 illustrates a cannula having three larger circular openings while cross-section BB, option 2 illustrates the cross-section farther along the cannula in which the cross-section is three smaller circular openings for delivering the liquid drug. Of course, the illustrated cross-sections are examples and other cross-sections may be used to deliver the liquid drug.

Figure 8:
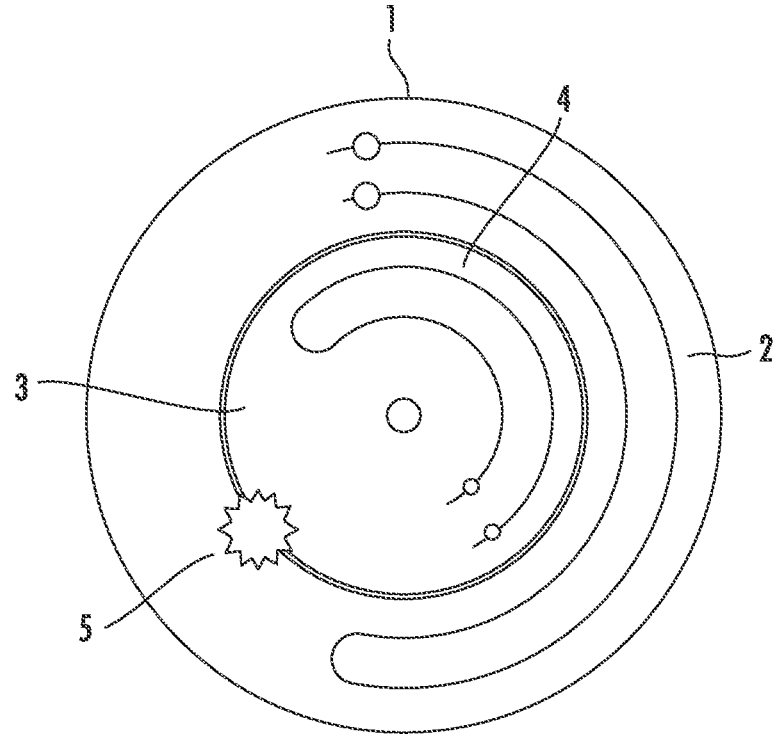
FIG. 8 illustrates an example of a flow regulator valve suitable for use in the example of FIG. 6.

FIG. 8 illustrates an exemplary example of a flow regulator valve suitable for use in the example of FIG. 6. An on-body pump device as described herein may include reservoirs for two fluids as described above. The pump system may deliver two different fluids at different times (e.g., insulin and glucagon), two different fluids at the same time that are mixed (e.g., drug mixing), or the same fluid at different times with different rates (e.g., insulin bolus and basal).

As shown in FIG. 8, the flow regulator valve 801 may embody two flow channels. For example, the flow regulator valve 801 may include a first flow channel 806 and a second flow channel 804. The two flow channels may be independently set or changed relative to one another via a gear system 805 (e.g., a planetary gear). For example, the gear system 805 may be configured to independently set a flow rate of the first fluid output from the first pump mechanism relative to a flow rate of the second fluid output from the second pump mechanism. As shown in FIG. 8, an inner valve 803 may have a separate flow channel 804 to deliver a first stored fluid (stored in a first reservoir, such as 606 of FIG. 6) at a first rate and the outer valve 802 may have separate flow channel 806 to deliver a second stored fluid (stored in a second reservoir, such as 607 of FIG. 6) at a second rate, independent of the first rate.

The following components may be included with example of the drug delivery system described herein (e.g., as shown in reference to FIGS. 1-8):

301/14—On-body pump device
  302—Activation switch
  303—Insertion mechanism button
  304—Insertion/retraction spring
  305—Removable secondary unit/assembly
  306—Settings dial
  307—Optional Prefilled cartridge
  308—Stop
  309—Fill needle
  310—Reservoir
  311—Corresponding activation component to activation switch (2)
  312—Needle/cannula
  313—fluid pathway
  315—Interlock device (e.g., to require filling prior to allowing insertion)
  316—Septum for insertion mechanism
  343—Septum for fill and/or settings configuration
  18—Release button
  319—Interlock device (e.g., to require insertion before allowing release)

Various examples described include a wearable drug delivery device capable of delivering one more liquid drugs (or any other fluid or therapeutic agent) to a user.

Certain examples of the present example were described above. It is, however, expressly noted that the present example is not limited to those examples, but rather the intention is that additions and modifications to what was expressly described herein are also included within the scope of the example. Moreover, it is to be understood that the features of the various examples described herein were not mutually exclusive and may exist in various combinations and permutations, even if such combinations or permutations were not made express herein, without departing from the spirit and scope of the example. In fact, variations, modifications, and other implementations of what was described herein will occur to those of ordinary skill in the art without departing from the spirit and the scope of the example. As such, the example is not to be defined only by the preceding illustrative description.

Various examples also relate to apparatus or systems for performing these operations. The suitable structure for a variety of these machines will appear from the description given.

It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, various features are grouped together in a single example for streamlining the disclosure. This method of disclosure is not to be interpreted as reflecting an intention that the claimed examples require more features than are expressly recited in each claim. Rather, as the following claims reflect, inventive subject matter lies in less than all features of a single disclosed example. Thus, the following claims are hereby incorporated into the Detailed Description, with each claim standing on its own as a separate example. In the appended claims, the terms "including" and "in which" are used as the plain-English equivalents of the respective terms "comprising" and "wherein," respectively. Moreover, the terms "first," "second," "third," and so forth, are used merely as labels and are not intended to impose numerical requirements on their objects.

What has been described above includes examples of the disclosed architecture. It is, of course, not possible to describe every conceivable combination of components and/or methodologies, but one of ordinary skill in the art may recognize that many further combinations and permutations are possible. Accordingly, the novel architecture is intended to embrace all such alterations, modifications, and variations that fall within the spirit and scope of the appended claims.

What is claimed is:

1. A system, comprising:
  an on-body pump device comprising a reservoir and a fluid pathway, wherein the reservoir is configured to hold fluid; and
  a secondary unit removably coupled to the on-body pump device and including a fill needle, a cartridge stop, and an opening;
  and a prefilled cartridge containing:
    a liquid drug; and
    a moveable plunger movable within the prefilled cartridge, to expel the liquid drug from the prefilled cartridge into the fill needle through a movement of the movable plunger in the prefilled cartridge as the prefilled cartridge is inserted into the opening, wherein the secondary unit is configured to:
    deliver the liquid drug to the reservoir of the on-body pump device via the fill needle; and
    wherein the secondary unit further comprises a second needle and a needle insertion mechanism, wherein the second needle is coupled to the fluid pathway, and the needle insertion mechanism is operable to insert the second needle into skin of a user to enable delivery of the liquid drug.

2. The system of claim 1, further comprising a first interlock operable to prevent operation of the needle insertion mechanism until the reservoir is filled with a desired volume of the liquid drug.

3. The system of claim 1, wherein the secondary unit further comprises:
  a first dial operable to select a basal rate for delivery of a basal dosage of the liquid drug; and
  a second dial operable to select a bolus increment for delivery of a bolus dosage of the liquid drug.

4. The system of claim 1, wherein the cartridge stop is configured to contact the movable plunger of the prefilled cartridge.

5. The system of claim 1, wherein the on-body pump device further comprises an introducing needle device operable to insert a needle coupled to the reservoir into skin of a user.

6. The system of claim 1, wherein the secondary unit further comprises a second opening configured to receive a second prefilled cartridge, wherein the first opening includes a first fill needle and the second opening includes a second fill needle.

7. The system of claim 6, wherein the reservoir comprises a first reservoir compartment and a second reservoir compartment, wherein:

the first reservoir compartment is fluidly coupled to the first fill needle within the first opening, and the second reservoir compartment is fluidly coupled to the second fill needle within the second opening.

8. A secondary unit, comprising:

an opening configured to receive a prefilled cartridge containing a liquid drug, wherein a fill needle and a cartridge stop are within the opening a needle insertion mechanism configured to actuate an introducing needle device of an on-body pump device; and a settings dial configured to set or adjust an amount of the liquid drug for delivery into the on-body pump device, wherein the fill needle has one end configured to pierce a septum of the on-body pump device to deliver the liquid drug to the on-body pump device and another end configured to pierce a movable plunger of the prefilled cartridge, wherein the liquid drug is expellable from the prefilled cartridge into the fill needle as the prefilled cartridge is inserted into the opening through a movement of the movable plunger in the prefilled cartridge to deliver the liquid drug to a reservoir of the on-body pump device via the fill needle.

9. The secondary unit of claim 8, wherein the needle insertion mechanism comprises:

an insertion mechanism button at a surface of the secondary unit, wherein the insertion mechanism button is operable to actuate the insertion mechanism;

an insertion spring responsive to actuation of the insertion mechanism button; and a member coupled to the insertion spring, wherein the member is configured to interact with a septum of the on-body pump device.

10. The secondary unit of claim 8, further comprising a variable fill mechanism coupled to the opening and operable to extract a volume of the liquid drug from a prefilled cartridge inserted in the opening, wherein the volume is variable based on a volume setting mechanism.

11. The secondary unit of claim 10, wherein the variable fill mechanism further comprises:

a visual indicator movable along a volume scale shown on a visual amount indicator component;

a gear operable to move the visual indicator to a desired volume of the liquid drug relative to the visual amount indicator component;

a needle operable to pierce a plunger within the prefilled cartridge to extract a volume of the liquid drug from a prefilled cartridge;

a variable fill rod operable to move as the prefilled cartridge is inserted in the opening;

a travel pin operable to engage the plunger and move as the prefilled cartridge is inserted in the opening, the travel pin configured to travel until intersecting with a travel stop having an inclined plane;

an indicator rod configured to show an amount of the desired volume of the liquid drug on the visual amount indicator component that has been output from the prefilled cartridge, wherein the indicator rod is contacted by the travel pin which pushes the indicator rod in a path indicating the amount of the desired volume; and a spring-loaded component operable to prevent the indicator rod from returning to a prior position.

12. The secondary unit of claim 8, further comprising a release button that enables the secondary unit to be removed from the on-body pump device.

* * * * *